United States Patent
Greenberg

(10) Patent No.: US 8,852,285 B2
(45) Date of Patent: Oct. 7, 2014

(54) PROSTHESIS FOR DISTAL RADIOULNAR JOINT

(75) Inventor: Jeffrey A Greenberg, Carmel, IN (US)

(73) Assignee: Jeffrey A Greenberg, Indianapolis, IN (US)

( * ) Notice: Subject to any disclaimer, the term of this patent is extended or adjusted under 35 U.S.C. 154(b) by 36 days.

(21) Appl. No.: 13/418,953

(22) Filed: Mar. 13, 2012

(65) Prior Publication Data

US 2013/0245778 A1 Sep. 19, 2013

(51) Int. Cl.
*A61F 2/42* (2006.01)

(52) U.S. Cl.
USPC ..................... 623/21.12; 623/21.11

(58) Field of Classification Search
CPC .......................................... A61F 2/42
USPC ..................... 623/20.11–20.13, 21.11–21.19; 606/86 R
IPC .......................................... A61F 2/42
See application file for complete search history.

(56) References Cited

U.S. PATENT DOCUMENTS

| | | |
|---|---|---|
| 4,714,476 A | 12/1987 | Ranawat et al. |
| 4,936,854 A | 6/1990 | Swanson |
| 5,108,444 A | 4/1992 | Branemark |
| 5,136,743 A | 8/1992 | Pirela-Cruz |
| 5,906,210 A | 5/1999 | Herbert |
| 5,938,699 A | 8/1999 | Campbell |
| 5,951,604 A | 9/1999 | Scheker |
| 6,284,000 B1 | 9/2001 | Ege |
| 6,302,915 B1 | 10/2001 | Cooney, III et al. |
| 6,656,225 B2 | 12/2003 | Martin |
| 7,722,676 B2 | 5/2010 | Hanson et al. |
| 7,766,970 B2 | 8/2010 | Shultz et al. |
| 7,875,082 B2 | 1/2011 | Naidu |
| 2003/0135280 A1 | 7/2003 | Kopylov et al. |
| 2010/0121390 A1* | 5/2010 | Kleinman ................... 606/86 R |
| 2011/0066250 A1 | 3/2011 | Palmer |

FOREIGN PATENT DOCUMENTS

WO WO 2006/060315 A1 6/2006

OTHER PUBLICATIONS

International Search Report and Written Opinion issued in PCT/US2013/029312, dated Jun. 26, 2013.

* cited by examiner

*Primary Examiner* — David Isabella
*Assistant Examiner* — Yashita Sharma
(74) *Attorney, Agent, or Firm* — Woodard, Emhardt, Moriarty, McNett & Henry LLP

(57) ABSTRACT

Among other things, there are disclosed embodiments of implants for repairing or relieving damage to the distal radioulnar joint. A component for replacing at least part of the ulnar head includes a concave surface for accommodating a convex surface of a component for attachment to the radius, e.g. in the sigmoid notch of the radius.

12 Claims, 5 Drawing Sheets

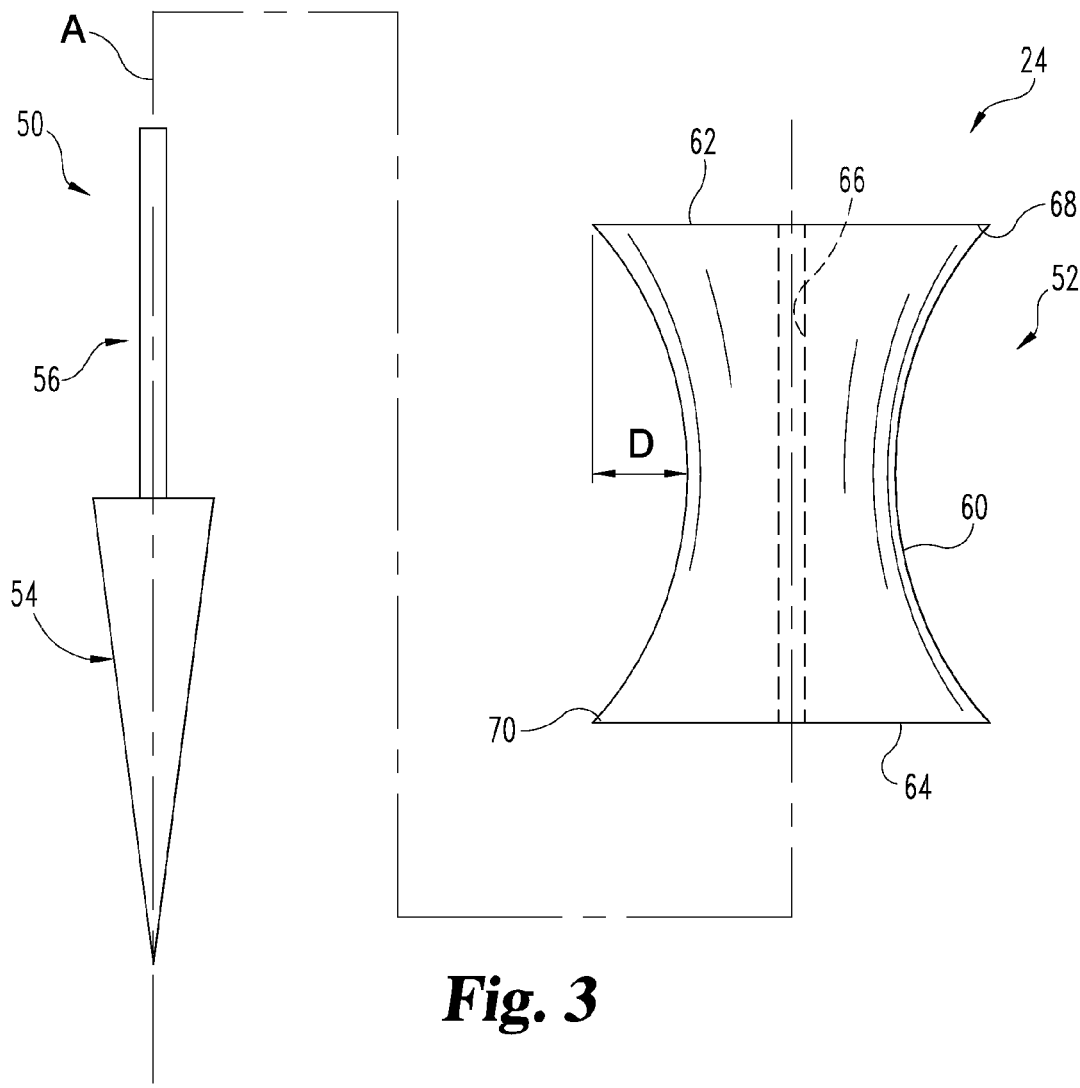

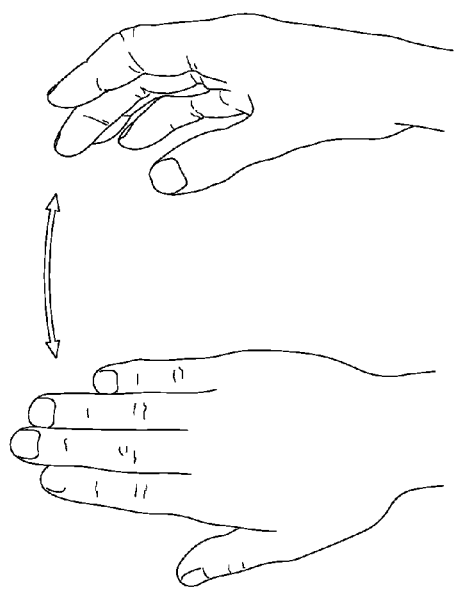
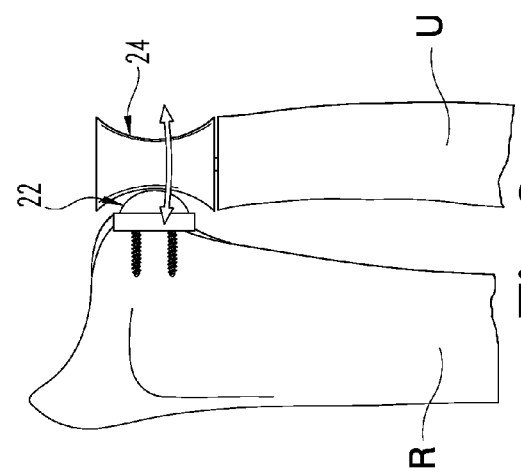
Fig. 8
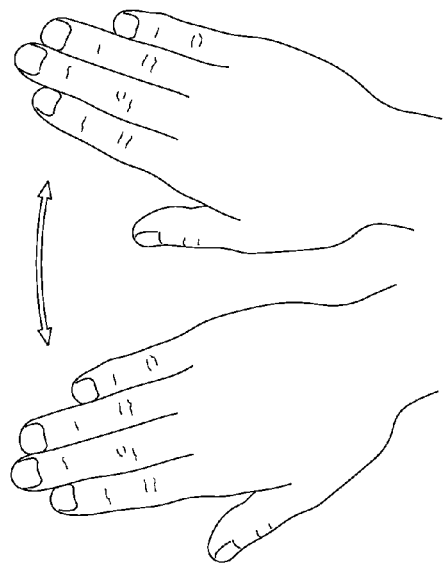
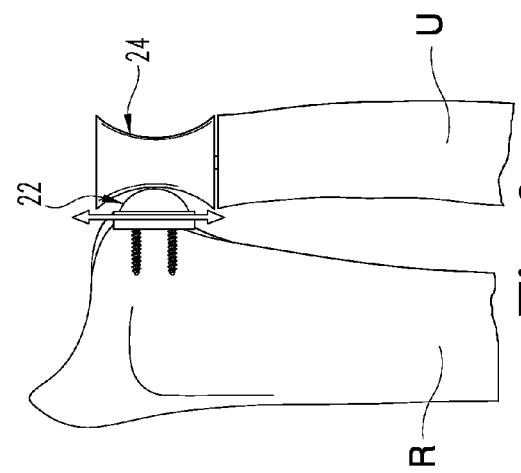
Fig. 9

PROSTHESIS FOR DISTAL RADIOULNAR JOINT

The present disclosure concerns orthopedic devices for corrective, therapeutic or other purposes in the wrist. In particular, this disclosure provides an implant system for replacing portions of the distal radioulnar joint to maintain or improve movement and usability of the joint.

BACKGROUND

The radius and ulna together form the bony structure of the forearm. These bones are linked and articulate with one another at both their proximal ends (at the elbow) and distal ends (at the wrist). The distal radioulnar joint (DRUJ) is a pivot joint adjacent the wrist, with the head of the ulna and sigmoid notch of the radius bone interacting so that the distal end of the radius articulates in pronation and supination on the distal head of the ulna. As seen in FIG. 1, the distal portion of the ulna U (i.e. that portion closer to the wrist and hand) has a head H with an articular surface AS and a styloid process SP, and the distal portion of the radius bone R includes a sigmoid notch N on its medial side. In a normal DRUJ, articular surface AS engages sigmoid notch N, and the DRUJ permits the familiar range of motion in pronation, supination and pivoting about axes substantially perpendicular to the radius and ulna bones. Fractures of the distal radius and/or ulna, other injuries of the forearm, diseases affecting the tissues or other maladies may affect the distal ends of the radius and/or ulna and cause rotational instability of the DRUJ. Ulnar styloid process fractures, and fractures into the distal radioulnar joint can occur with such injuries or other trauma. Fracture or dislocation involving the DRUJ can result in a loss of forearm rotation related to either instability or incongruity between the mating parts of the distal radius and ulna.

With severe injuries to the DRUJ or other loss of its stability, loss of the ability to rotate the forearm (pronation and supination) as well as weakness in the individual's grip and/or pinch can occur. Treatments for damage to the distal radius or ulna and/or correction of the DRUJ have been proposed using hemiarthroplasty, which features resection of the head of the ulna and replacement with a prosthesis. Such prostheses contact the sigmoid notch of the radius bone directly to allow some pivoting, in a way approximating the natural configuration of the joint. However, contact between a prosthesis and natural bone can unnaturally wear the bone tissue, potentially leading to damage to the sigmoid notch or other part of the radius bone, an arthritis condition, or other degenerative change. Accordingly, reinforcements for the sigmoid notch in the form of a plate or similar implant covering the notch have been used. These items are designed to keep the ulnar prosthesis applied in hemiarthroplasty from contacting bone. That solution derives from a desire to maintain the notch or similar structure in the radius bone. It also derives from an interest in maintaining most or all of the head of the radius bone intact.

Other types implants have been proposed to replace surfaces of both the ulna and the radius bones. However, existing implants still suffer significant lack of stability and/or mobility in the joint. Accordingly, there is a need for a prosthetic device that provides greater stability and mobility in repairing a damaged DRUJ.

SUMMARY

Among other things, there is disclosed systems, apparatus and methods for replacing at least a portion of the distal radio-ulnar joint. In some embodiments, a system includes a first component for attachment to a distal portion of a patient's radius bone, and a second component for attachment to a distal portion of a patient's ulna so as to substantially face the first component. The first component has a convex outer surface portion having a first radius of curvature to be directed substantially away from the radius bone, and an opposite surface configured differently from the convex outer surface portion. At least one prong extends from the opposite surface for insertion into the radius bone, whereby the first component is fixed to the radius bone. The second component has a concave outer surface with a second radius of curvature greater than the first radius of curvature and a second surface that is non-continuous with the concave outer surface for facing a portion of the ulna. When implanted, the convex outer surface portion of the first component lies adjacent or in contact with the concave outer surface of the second component, a longitudinal axis of the second component is substantially parallel to the patient's ulna, and the first component is capable of travel with respect to the second component in rotation substantially around the longitudinal axis and in translation substantially along the direction of the longitudinal axis.

Particular embodiments of the components are also provided. For example, the concave outer surface portion of the second component can be substantially uniform and continuous around at least half of the circumference of the second component, or around substantially all of the circumference of said second component. In such cases, a cross section of the second component along the longitudinal axis may have substantially the shape of a biconcave lens. The concave surface of the second component may be substantially in the shape of a portion of a circle turned around an axis that is substantially parallel to a central tangent to the concave surface. Further, the second component is adapted to be rotatable around the longitudinal axis after implantation in some embodiments. For instance, the second component can be mounted on an axle that has a portion for mounting into the patient's ulna. The axle is thus fixed with respect to the ulna while the second component is rotatable around the axle. One or more prongs can be connected to the second component, for secure fixation with the patient's ulna.

Embodiments of systems or devices to replace at least a portion of the distal radio-ulnar joint as described herein can include an ulnar element for attachment to the distal end of an ulna. The ulnar element includes an fixing component having a portion for insertion into an ulna and an axle portion with a longitudinal axis and extending from the portion for insertion. The ulnar element further includes a bearing component having an external concave surface and a central opening. The axle portion of the fixing component extends at least part-way through the central opening so that the bearing component can rotate with respect to said axle portion around the axis. A radial element, for attachment to the distal end of a radius so that the radial element faces the ulnar element, has a convex portion with a radius of curvature smaller than a largest dimension of the external concave surface.

In particular embodiments, the radial element includes at least one prong facing oppositely from the convex portion. The prongs are adapted to be inserted into a radius bone for fixing the radial element to the bone in an orientation such that the convex portion of the radial component faces the concave surface of the ulnar component. The radial element can include a substantially flat surface opposite the convex portion, from which substantially flat surface the prong(s) extend. Such a substantially flat opposite surface can be part or substantially all of a separate piece into which a piece including the convex portion snaps or is otherwise fitted into.

In some embodiments, the external concave surface of the ulnar element extends around the axis at least about 90 degrees. The ulnar element can also include a non-concave surface opposite the concave external surface and a bottom surface adjacent both the concave external surface and opposite non-concave surface. The opposite surface and bottom surface are adapted to fit closely to respective surfaces of an ulna. At least one of such a non-concave surface and/or bottom surface can include a portion for insertion into and fixation with an ulna.

Methods for implantation of the devices and systems described herein are also disclosed. These devices and methods provide a more stable replacement for the distal radioulnar joint, with a greater range of movement, than existing devices. It is believed that systems and methods as disclosed herein provide a full or better range of motion, while departing from the idea of patterning a DRUJ prosthesis after natural structures.

BRIEF DESCRIPTION OF THE DRAWINGS

FIG. 2 is an elevational view of an embodiment of a component in a prosthetic system for replacement of a distal radioulnar joint.

FIG. 3 is an exploded elevational view of an embodiment of another component, for use with the embodiment in FIG. 2, in a prosthetic system for replacement of a distal radioulnar joint.

FIG. 8 is a representation of general movement of the hand and forearm in pronation and supination, with a representation of the general movement of an embodiment of a prosthesis for replacement of the distal radioulnar joint corresponding to such pronation and supination.

FIG. 9 is a representation of general movement of the hand and forearm in pivoting around an axis generally perpendicular to the page, with a representation of the general movement of an embodiment of a prosthesis for replacement of the distal radioulnar joint corresponding to such pivoting.

DESCRIPTION OF THE ILLUSTRATED EMBODIMENTS

Reference will now be made to certain embodiments and specific language will be used to describe the same. It will nevertheless be understood that no limitation of the scope of this disclosure and the claims is thereby intended, such alterations, further modifications and further applications of the principles described herein being contemplated as would normally occur to one skilled in the art to which this disclosure relates.

Referring generally to the Figures, there are shown embodiments of a two-component implant system 20 for repairing or relieving effects of damage to the distal radioulnar joint (DRUJ). Generally speaking, system 20 includes a component 22 for attachment to a distal portion of the radius bone, and a component 24 for attachment to a distal portion of the ulna so that components 22, 24 substantially face each other generally in contact. Because of the subject matter herein, concerning both a bone and a geometric entity (or its length) known as a "radius," the term "radius bone" will generally be used to refer to the bone, and where possible an appropriate explanatory term will be added to geometric use of "radius" (e.g. "radius of curvature"). Such terms added to "radius" are intended simply to distinguish those two usages (anatomic versus geometric) herein, and are not intended to otherwise limit use or meaning of "radius."

Figure 1:
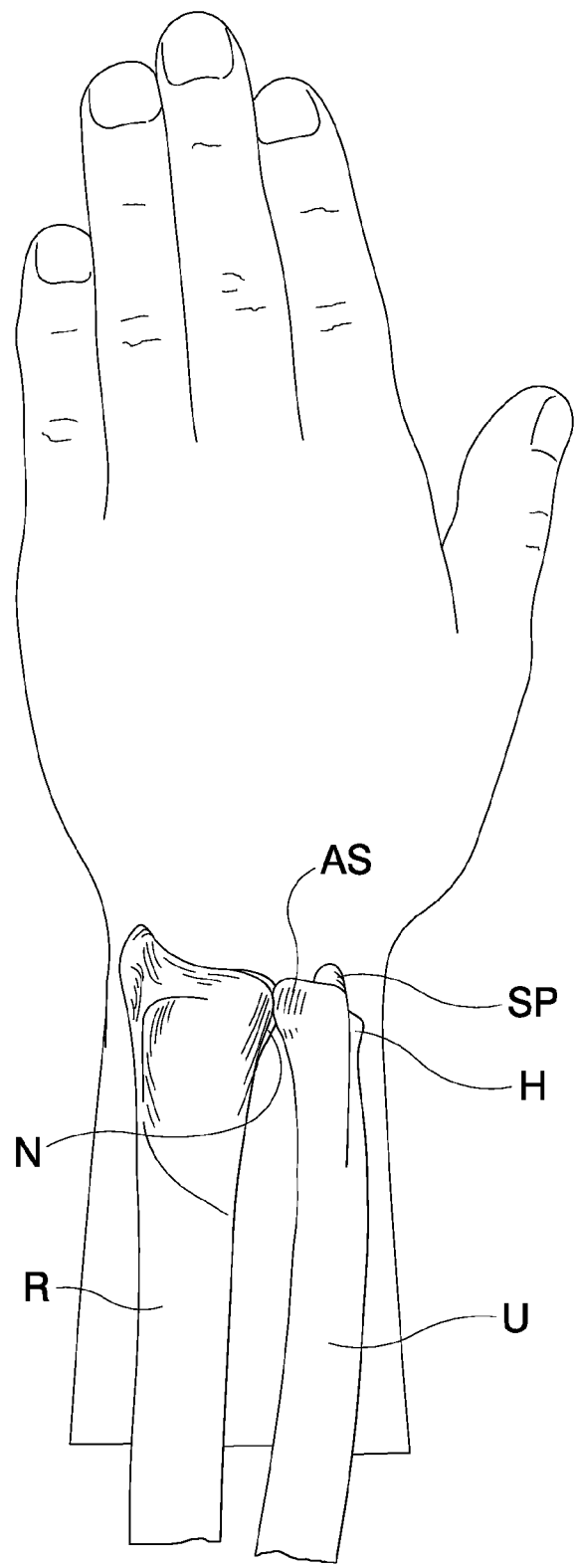
FIG. 1 is a representation of a natural distal portion of the forearm, showing the relationship between the radius and ulna bones in relation to the wrist and hand.
Figure 4:
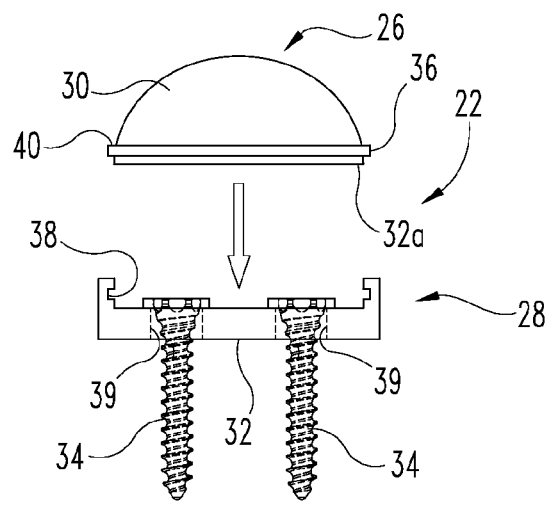
FIG. 4 is an elevational view of another embodiment of the component of FIG. 2.

The illustrated embodiment of component 22 has a convex portion 26 and a base portion 28. Convex portion 26 has an external convex surface 30 which may be part-spherical or configured as a geometric segment of a sphere. Base portion 28 includes a surface 32 opposite to convex surface 30 for facing or contacting the radius bone. One or more prongs or extensions 34 for insertion into the bone are connected to or through one or both of portions 26, 28. Use of more than one prong 34 tends to limit or eliminate rotation of component 22 or base 28 around a prong 34 with respect to bone. Component 22 may be a unitary item, i.e. with each of portions 26, 28 being a part of a single item, and extension(s) 34 also a part of that single item. In other embodiments (e.g. FIG. 4), convex portion 26 is separate initially from base 28, onto or into which portion 26 fits, e.g. in an interference, threaded or snap fit. For instance, portion 26 or a part of it (such as a rib, thread or tongue 36) may turn or snap into a groove or indentation 38 in base 28. In such a case, base 28 may include one or more holes 39 through which prong(s) 34 extend, particularly if prong(s) 34 are threaded (e.g. FIG. 4). Threaded prong(s) 34 may be fashioned as screws, as indicated below. Portion 26 may be thought of in this embodiment as a spherical segment or male part that fits or snaps into an opening in a disc-like base 28.

Convex surface 30 is shown as a substantially spherical surface having a predetermined radius of curvature. In that embodiment, portion 26 may be geometrically thought of as a segment of a sphere that adjoins base 28. Surface 30 is limited by an edge or perimeter 40 that defines a geometric small circle (i.e. a circle formed by the intersection of a plane and a sphere but not along a diameter of the sphere) in this embodiment. In other embodiments, the configuration of surface 30 need not be spherical, but may be ellipsoidal, catenoidal, paraboloidal or other curved convex configurations that will permit smooth movements of surface 30 with respect to component 24, as will be discussed further below.

Base portion 28 is substantially cylindrical or disc-like in this embodiment, while in other embodiments it may have a rectilinear (e.g. square) outer configuration. In embodiments in which portions 26 and 28 are separate, a planar surface 32a may be opposite surface 30. Surface 32 is configured for positioning in contact with a distal portion of the radius, e.g. within or in place of the sigmoid notch of the radius bone. The illustrated embodiment of surface 32 is substantially flat for flush placement against a prepared flat surface of the radius bone, as will be discussed further below. In other embodiments, a non-flat surface 32 may be provided, such as a substantially part-cylindrical or other convex surface to fit closely with the natural surface of the sigmoid notch, or a portion of the sigmoid notch that has been rounded or prepared for such a surface 32.

Prongs or extensions 34 are intended for insertion into the distal end of the radius bone, non-parallel to the axis of the bone in a particular embodiment, and to fix component 22 with respect to the bone. In particular embodiments, prongs 34 are sharp or pointed extensions that are inserted into the radius bone to hold component 22 to it. Prongs 34 may be unitary or otherwise fixed with component 22. For example, prongs 34 may be fixed to surface 32 of base portion 28 to extend substantially in a direction opposite from surface 30 of portion 26. It will be understood that prongs 34 may have a conical external surface that widens toward surface 32, so as to make an interference fit with the bone. Alternatively, notches or tabs on prongs 34 may be provided in order to improve purchase within the bone. In other embodiments, prongs 34 may be initially separate from component 22 or at least one of parts 26, 28 and then inserted through one or both of parts 26, 28. For example, in such embodiments prongs 34 in the form of screws may be inserted through base 28 and surface 32 (e.g. FIG. 4), with a portion (e.g. a head portion) of each such screw abutting a portion (e.g. an internal boss or ledge around a hole) of base 28 to anchor component 22 to the bone. It will be appreciated that in other embodiments, screws or other prongs 34 may be inserted through or fixed to surface 30 or other part of portion 26 as well.

Component 24 includes a shaft portion 50 and a receiving portion 52 that is mounted on shaft 50 so as to receive component 22 during or after implantation. Shaft 50 includes an insertion portion 54 adapted to be anchored within the ulna. In a particular embodiment, insertion portion 54 is substantially conical to create an interference fit within a hole drilled in the bone. In other embodiments, a series of notches or tabs may be provided on insertion portion 54 to improve purchase with bone tissue after insertion. In another example, insertion portion may be threaded so as to twist or screw into the tissue of the ulna. In such embodiments, internal or external driving surfaces may be provided on or for shaft 50. Shaft 50 also includes an extension portion 56 connected to insertion portion 54, so that when insertion portion 54 is anchored to the ulna, extension portion 56 is partially or entirely exposed from the bone. In the illustrated embodiment, extension portion 56 is substantially cylindrical and has a diameter substantially smaller than that of some or all of insertion portion 54. Further, that embodiment shows extension portion 56 and insertion portion 54 having a common central longitudinal axis A. While a particular embodiment of shaft 50 is unitary (i.e. one-piece), it will be understood that other embodiments may have an extension portion 56 fitted into or assembled with a separate insertion portion 54.

The illustrated embodiment of receiving portion 52 is substantially in the form of a block having a concave lateral surface 60, top or distal surface 62, bottom or proximal surface 64, and a channel 66 between and extending through surfaces 62 and 64. Concave surface 60 may be generally in the form of a bowl or crater-like depression along a lateral part of receiving portion 52. In the illustrated embodiment, concave surface 60 extends at least part way around the outside of receiving portion 52, defining a curved or part-spherical surface turned around the central longitudinal axis of receiving portion 52. Surface 60 may extend entirely around receiving portion 52, or may extend around a limited portion, e.g. 90 degrees, 180 degrees or 270 degrees, depending on the amount of mobility available or desired in the distal radioulnar joint. Top or distal surface 62 is planar in the illustrated embodiment, and generally faces the hand when implanted. Bottom or proximal surface 64 is likewise planar as illustrated and generally faces the ulna when implanted. A lip or edge 68 is provided at the intersection of top surface 62 and concave surface 60, and a lip or edge 70 is provided at the intersection of bottom surface 64 and concave surface 60. The depth D of surface 60 at its greatest is measured perpendicular to a central longitudinal axis, from the point on surface 60 closest to the central longitudinal axis out to the furthest extent of surfaces 62 and/or 64 from the central longitudinal axis. Depth D of receiving portion 52 is such that at least part of portion 26 of component 22 not only enters but is contained within the limits of surface 60 and edges 68, 70 on implantation, as will be discussed further below.

Surface 60 has a curvature that allows not only relative movement of component 22 around the longitudinal axis of receiving portion 52 (relative rotation), but also allows a small amount of relative translation of component 22 longitudinally, i.e. generally toward edges 68, 70. In other words, the curvature of surface 60 in some embodiments allows relative motion between component 22 and receiving portion 52, such relative motion having components in the rotational direction (around the longitudinal axis of receiving portion 52) and/or parallel to that longitudinal axis. As one example, where surface 60 has a substantially spherical or circular curvature (as cut by a plane containing the central longitudinal axis of receiving portion 52), the radius of curvature of surface 60 is slightly larger than a radius of curvature of surface 30. That larger radius of curvature allows component 22 and its surface 30 to move around and pivot within and with respect to surface 60, while also allowing some travel of component 22 and surface 30 toward or away from edges 68, 70. In this way, a full or wider range of motion for the distal radioulnar joint is provided.

Channel 66 in the illustrated embodiment lies along the central longitudinal axis and has an opening through both top surface 62 and bottom surface 64. It is substantially cylindrical and of approximately the same or slightly larger diameter than extension portion 56 of shaft portion 50. Extension portion 56 is inserted into channel 66, either prior to or during implantation, and may have a close or interference fit (if the diameters of channel 66 and extension portion 56 are substantially the same) or may permit rotation of receiving portion 52 around extension portion 56 (if the diameter of channel 66 is larger than that of extension portion 56). With receiving portion 52 assembled to extension portion 56 as noted, bottom surface 64 of receiving portion 52 generally faces insertion portion 54 of shaft 50, and when implanted bottom portion 64 generally faces or contacts ulnar bone tissue.

In use, embodiments of system 20 are implanted to provide a prosthetic for a distal radioulnar joint that provides better mobility and ease of use than existing devices. For example, in cases of trauma, malformation, removal of bone tissue as a treatment for disease, or other indications, system 20 can be implanted to permit continued use of the wrist joint in both pronation and supination.

Figure 5:
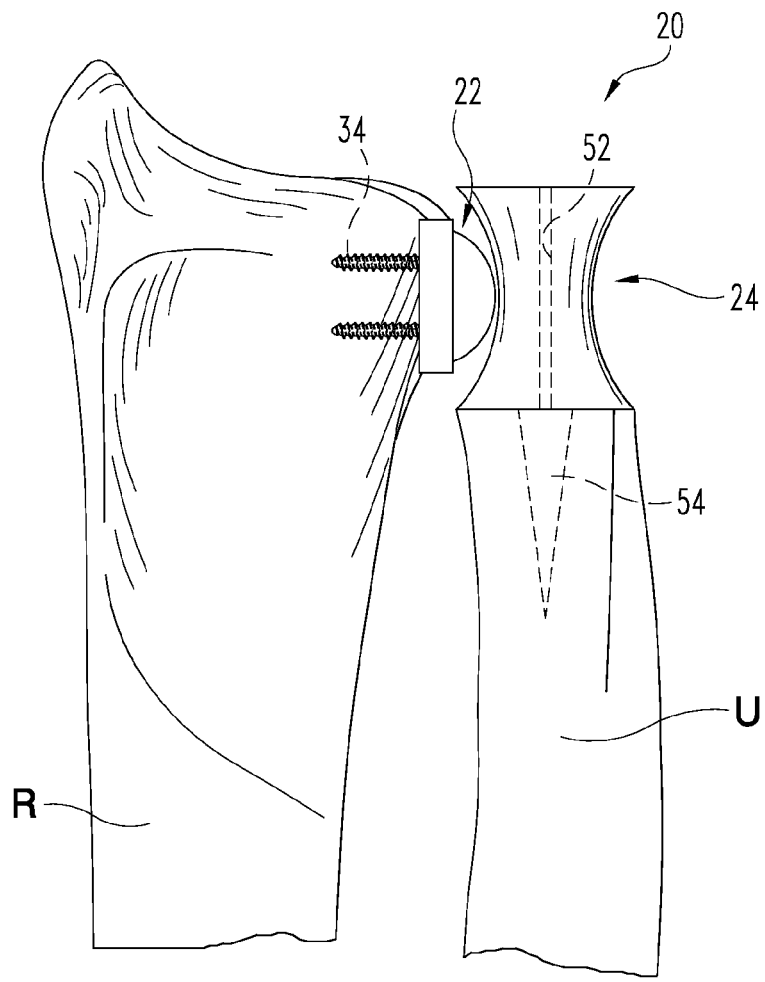
FIG. 5 is a representation of right radius and ulna bones viewed posteriorly with an embodiment of a prosthetic system for replacement of the distal radioulnar joint.

Surgical access to the distal radioulnar joint is first obtained via open or percutaneous routes. To the extent necessary, the surgeon may remove soft tissues, bone or other tissues that are too traumatized to remain or are otherwise indicated for removal. The surgeon prepares the radius bone R and/or the ulna U for system 20 as needed. For example, a portion of the sigmoid notch in the distal radius bone may be smoothed, abraded, resected or otherwise formed or treated for acceptance of component 22. For embodiments of component 22 in which surface 32 is substantially planar, a planar portion within or adjacent to the sigmoid notch may be prepared. The example in FIG. 5 shows substantially all of the portion of the radius bone around the sigmoid notch resected to provide a region or pocket with flat surfaces in which component 22 is placed. For embodiments in which surface 32 is rounded or otherwise configured, an appropriate surface configuration for the radius bone can be created. Similarly, the distal portion of the ulna U may be treated for acceptance of component 24. In the illustrations in FIGS. 5, 8 and 9, all or substantially all of the head of the ulna is removed, leaving a substantially flat surface through which component 24 is attached to the ulna.

With the bones prepared as necessary, components 22 and 24 of system 20 are fixed to the bones. Component 22 is fixed to a lateral portion of the radius bone (e.g. a portion prepared as noted above) in the general area of the sigmoid notch or where the notch had previously been, so that convex surface 30 of component 22 generally faces the ulna. Prong(s) 34 are inserted into the radius bone so that prong(s) 34 generally point toward the longitudinal axis of the bone. If necessary, one or more holes are drilled to accommodate prong(s) 34. In embodiments in which prong(s) 34 are conical or include notches and/or tabs, component 22 may be directly pushed in, while in embodiments in which prong(s) 34 are screws, they are threaded into the bone. In embodiments in which surface 30 and 32 are on separate parts (e.g. segment or portion 26 and base 28), base 28 can be attached to the radius bone first, fixed via screws or other prong(s) 34, and segment 26 is snapped into or otherwise fixedly fitted to base 28.

Component 24 is fixed to the ulna. Insertion portion 54 of shaft part 50 is inserted into the ulna substantially parallel to or along the longitudinal axis of the ulna. In the illustrated embodiment, in which the entire head of the ulna is removed leaving a substantially flat bone surface, insertion portion 54 is inserted through that flat bone surface and into the bone. The surgeon may drill or otherwise prepare a hole into the bone for insertion portion 54, to ease the insertion (e.g. by direct force or through threading insertion portion 54 into such a hole). With insertion portion 54 inserted fully or partially in the ulna, extension portion 56 remains outside the bone, and in this embodiment its longitudinal axis is generally parallel to or along the longitudinal axis of the bone.

Receiving part 52 is either pre-assembled to extension portion 56 or is placed on extension portion 56 after shaft 50 is inserted into the ulna bone. In either situation, extension portion 56 extends all or part of the way through channel 66 in receiving portion 52. As noted above, in some embodiments receiving part 52 is rotatable around extension portion 56, while in others a close, interference or locking fit between receiving part 52 and extension portion 56 is created. Regardless of how and when receiving part 52 is assembled with shaft 50, component 24 is fixed to the ulna so that concave exterior surface 60 of receiving part 52 generally faces the sigmoid notch of the radius bone and component 22 fixed to the radius bone.

Either component 22 or component 24 may be fixed to its respective bone before the other, or they may be fixed to their respective bones substantially simultaneously. When the implantation is complete, components 22 and 24 are positioned with respect to each other so that a portion of convex surface 30 of component 22 is in contact with concave surface 60 of receiving portion 52 of component 24. Some or all of convex surface 30 remains in the space defined by concave surface 60 (e.g. part of convex surface 30 remains in contact with concave surface 60, while one or both components move with respect to each other. As the forearm rotates in pronation or supination (FIG. 8), the radius bone and the ulna rotate with respect to each other, and components 22 and 24 rotate with respect to each other, e.g., component 22 travels generally around the central longitudinal axis of component 24 (shaft 50 and receiving portion 52). As the hand or wrist twists left or right around an axis substantially perpendicular to the distal radioulnar joint (FIG. 9), components 22 and 24 translate substantially along the longitudinal axis of shaft 50 with respect to each other. Such translation is limited by contact between surfaces 30 and 60 and/or by contact between component 22 (e.g. surface 30 or base 28) and one of the edges 68, 70 of receiving portion 52. Accordingly, either full or partial range of motion in all varieties of motion of the wrist are possible with embodiments of system 20.

Once components 22 and 24 are implanted as indicated above, any additional repair, replacement or rearrangement of soft tissues (e.g. ligaments, tendons, and/or cartilage) that may be necessary is performed. Additional treatments or medicaments, such as bone cements, oncological treatments, anti-infection agents, healing agents or the like, may also be applied or implanted. When all desired surgical treatments have been completed, the surgical opening is closed, and any appropriate topical or other dressings may be applied.

Figure 6:
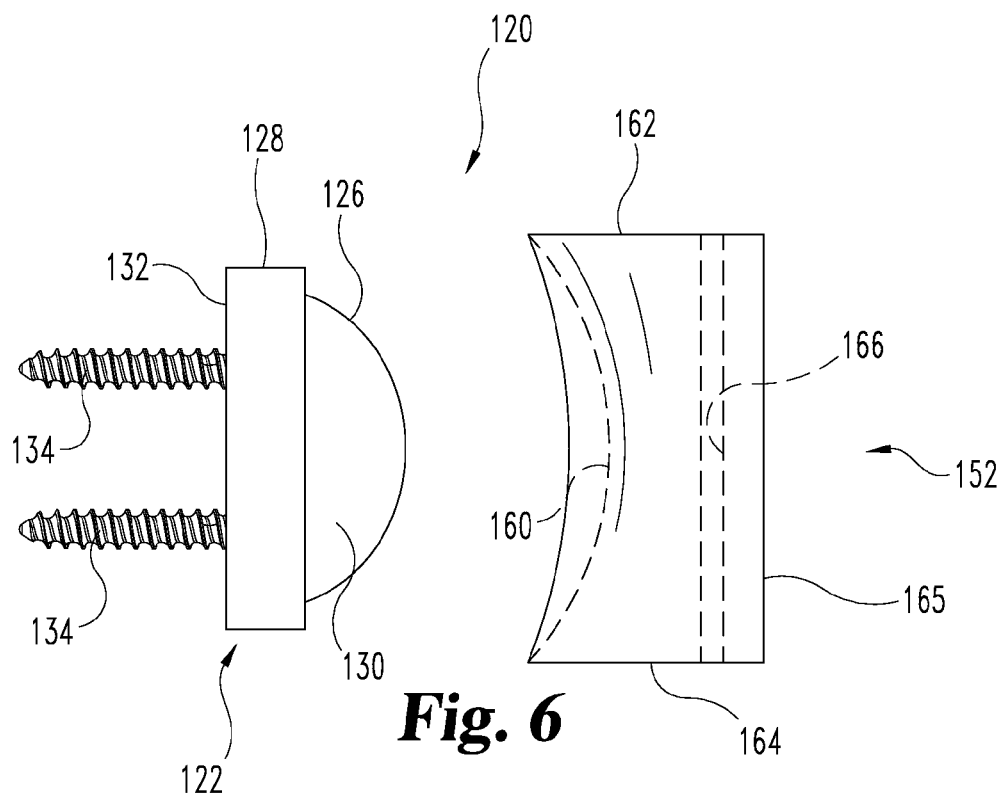
FIG. 6 is an elevational view of embodiments of components similar to those in FIGS. 2-4 in a prosthetic system for replacement of a distal radioulnar joint.
Figure 7:
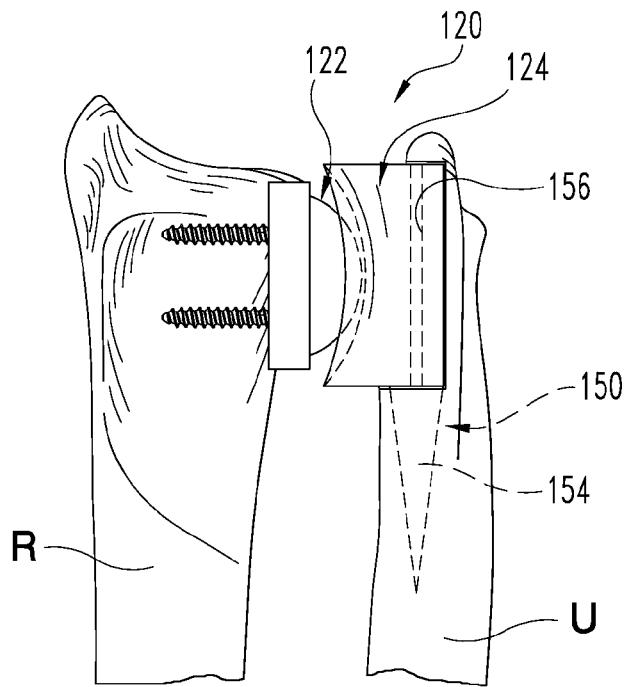
FIG. 7 is a representation of right radius and ulna bones viewed posteriorly with an embodiment as in FIG. 6 of a prosthetic system for replacement of the distal radioulnar joint.

FIGS. 6-7 represent a similar type of implant system 120 featuring a radius bone component 122 and an ulnar component 124. In the description below, items will be described that are similar or identical to items noted above, and such similar or identical items will be denoted with identical numbers as are used above along with the prefix 1.

Generally speaking, component 122 is an embodiment of component 22 as described above, having a segment portion 126 with a convex (e.g. part-spherical) surface 130, a base 128 with an opposite bone-facing or -adjoining surface 132, and one or more prongs 134. Likewise, portion 150 is substantially similar or identical to portion 50 described above, having an insertion portion 154 and an extension portion 156.

Receiving portion 152 has a block form, with a concave side surface 160, top surface 162, bottom surface 164, and a channel 166 between and extending through surfaces 162 and 164, similar to component 52. Where component 52 has a concave surface 60 that extends around the central longitudinal axis of component 52, concave surface 160 is a more bowl-like surface, or extends at most 45 to 135 degrees around the central longitudinal axis of component 124. An opposing bone-facing surface 165 is provided, which in the illustrated embodiment is substantially flat or planar (as are surfaces 162 and 164). Channel 166 is formed through receiving portion 152, with openings through one or both of surfaces 162 and 164, but in this embodiment channel 166 is laterally offset from a central longitudinal axis of receiving portion 152.

System 120 is used in cases in which it is unnecessary or undesirable to remove the entire ulnar head, and in which a portion of the ulnar head can be resected to provide a ledge for placement of component 124. For example, in FIG. 7 the ulna U has or is formed to have a wall W substantially parallel to the longitudinal axis of the ulna and a ledge L substantially perpendicular to wall W. Implantation of system 120 is substantially similar to that described above with respect to system 20. Insertion portion 154 is inserted into bone of the ulna through ledge L, at a position so that surface 165 is closely adjacent or in contact with wall W and surface 164 is closely adjacent or in contact with ledge L.

Preferred embodiments use sturdy biocompatible materials. Suitable materials may be or include metals (e.g. stainless steel, titanium), hard plastics, or other relatively rigid materials. As the implant systems described above are intended for permanent placement and use over a substantial period of years, non-resorbable materials should be used for the parts described above.

While the disclosure has been illustrated and described in detail in the drawings and foregoing description, the same is to be considered as illustrative and not restrictive in character, it being understood that only certain specific embodiments have been shown and that all changes and modifications that come within the spirit of the disclosure are desired to be protected. It is to be understood that structures or embodiments described in one context or with respect to one component may be used in other contexts or with respect to other components.

What is claimed is:

1. A system to replace at least a portion of the distal radio-ulnar joint, comprising:
   a first component for attachment to a distal portion of a patient's radius bone, said first component having a convex outer surface portion having a first radius of curvature to be directed substantially away from the radius bone and an opposite surface configured differently from said convex outer surface portion, and having at least one prong extending from said opposite surface for insertion into the radius bone, whereby the first component is fixed to the radius bone; and
   a second component for attachment to a distal portion of a patient's ulna so as substantially to face said first component, said second component having a concave outer surface with a second radius of curvature greater than said first radius of curvature and a second surface non-continuous with said concave outer surface for facing a portion of the ulna, said second component having a longitudinal axis extending through the second component,
   wherein when implanted, said convex outer surface portion of said first component lies adjacent or in contact with said concave outer surface of said second component, said longitudinal axis is substantially parallel to the patient's ulna, and said first component is capable of travel with respect to said second component in rotation substantially around said longitudinal axis and in translation substantially along the direction of said longitudinal axis.

2. The system of claim 1, wherein said concave outer surface of said second component is substantially uniform and continuous around at least half of the circumference of said second component, the circumference being around said longitudinal axis.

3. The system of claim 1, wherein said concave outer surface of said second component is substantially uniform and continuous around substantially all of the circumference of said second component, the circumference being around said longitudinal axis.

4. A system to replace at least a portion of the distal radio-ulnar joint, comprising:
   a first component for attachment to a distal portion of a patient's radius bone, said first component having a convex outer surface portion having a first radius of curvature to be directed substantially away from the radius bone and an opposite surface configured differently from said convex outer surface portion, and having at least one prong extending from said opposite surface for insertion into the radius bone, whereby the first component is fixed to the radius bone; and
   a second component for attachment to a distal portion of a patient's ulna so as substantially to face said first component, said second component having a concave outer surface with a second radius of curvature greater than said first radius of curvature and a second surface non-continuous with said concave outer surface for facing a portion of the ulna, said second component having a longitudinal axis,
   wherein when implanted, said convex outer surface portion of said first component lies adjacent or in contact with said concave outer surface of said second component, said longitudinal axis is substantially parallel to the patient's ulna, and said first component is capable of travel with respect to said second component in rotation substantially around said longitudinal axis and in translation substantially along the direction of said longitudinal axis; and,
   wherein a cross section of said second component along said longitudinal axis is substantially in the shape of a biconcave lens.

5. The system of claim 1, wherein said concave outer surface of said second component is substantially in the shape of a portion of a circle turned around an axis that is substantially parallel to a central tangent to said concave surface.

6. A system to replace at least a portion of the distal radio-ulnar joint, comprising:
   a first component for attachment to a distal portion of a patient's radius bone, said first component having a convex outer surface portion having a first radius of curvature to be directed substantially away from the radius bone and an opposite surface configured differently from said convex outer surface portion, and having at least one prong extending from said opposite surface for insertion into the radius bone, whereby the first component is fixed to the radius bone; and
   a second component for attachment to a distal portion of a patient's ulna so as substantially to face said first component, said second component having a concave outer surface with a second radius of curvature greater than said first radius of curvature and a second surface non-continuous with said concave outer surface for facing a portion of the ulna, said second component having a longitudinal axis extending through the second component,
   wherein when implanted, said convex outer surface portion of said first component lies adjacent or in contact with said concave outer surface of said second component, said longitudinal axis is substantially parallel to the patient's ulna, and said first component is capable of travel with respect to said second component in rotation substantially around said longitudinal axis and in translation substantially along the direction of said longitudinal axis; and,
   wherein said second component is adapted to be rotatable around said longitudinal axis after implantation.

7. The system of claim 6, wherein said second component is mounted on an axle, said axle having a portion for mounting into the patient's ulna so that said axle is fixed with respect to the ulna while said second component is rotatable around said axle.

8. The system of claim 1, further comprising a prong connected to said second component, said prong adapted for secure fixation with the patient's ulna.

9. The system of claim 1, wherein said opposite surface of said first component is substantially flat.

10. The system of claim 9, wherein said substantially flat opposite surface is a separate piece from said convex outer surface portion and wherein said convex outer surface portion snaps into said opposite surface.

11. The system of claim 6, wherein said concave outer surface of said second component is substantially uniform and continuous around at least half of the circumference of said second component around said longitudinal axis.

12. The system of claim 6, wherein said concave outer surface of said second component is substantially uniform and continuous around substantially all of the circumference of said second component around said longitudinal axis.

* * * * *